United States Patent
Peters et al.

(10) Patent No.: US 10,035,803 B2
(45) Date of Patent: Jul. 31, 2018

(54) SYNTHESIS OF COPANLISIB AND ITS DIHYDROCHLORIDE SALT

(71) Applicant: Bayer Pharma Aktiengesellschaft, Berlin (DE)

(72) Inventors: Jan-Georg Peters, Solingen (DE); Jürgen Stiehl, Sprockhövel (DE); Kai Lovis, Düsseldorf (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 15/524,478

(22) PCT Filed: Nov. 5, 2015

(86) PCT No.: PCT/EP2015/075765
§ 371 (c)(1),
(2) Date: May 4, 2017

(87) PCT Pub. No.: WO2016/071426
PCT Pub. Date: May 12, 2016

(65) Prior Publication Data
US 2017/0327505 A1    Nov. 16, 2017

(30) Foreign Application Priority Data
Nov. 7, 2014   (EP) .................................. 14192202

(51) Int. Cl.
*C07D 487/04* (2006.01)
*C07D 233/24* (2006.01)
*C07D 295/088* (2006.01)
*C07D 265/30* (2006.01)

(52) U.S. Cl.
CPC ......... *C07D 487/04* (2013.01); *C07D 265/30* (2013.01); *C07D 295/088* (2013.01)

(58) Field of Classification Search
CPC . C07D 487/04; C07D 295/088; C07D 233/04
USPC .................................................. 544/122, 250
See application file for complete search history.

(56) References Cited

U.S. PATENT DOCUMENTS

| 7,511,041 B2 | 3/2009 | Shimada et al. |
| 8,129,386 B2 | 3/2012 | Shimada et al. |
| 8,466,289 B2 | 6/2013 | Bock et al. |
| 2014/0072529 A1 | 3/2014 | Peters et al. |

FOREIGN PATENT DOCUMENTS

| WO | WO-2004/029055 A1 | 4/2004 |
| WO | WO-2008/070150 A1 | 6/2008 |
| WO | WO-2012/136553 A1 | 10/2012 |

OTHER PUBLICATIONS

Fujioka et al. "One-pot synthesis of imidazolines from aldehydes: detailed study about solvents and substrates," *Tetrahedron* 63(3): 638-643.
International Search Report dated Feb. 9, 2016, for PCT/EP2015/075765, filed Nov. 5, 2015, three pages.
U.S. Appl. No. 15/398,916, filed Jan. 5, 2017, for Hentemann et al. (U.S. Patent Application is not submitted herewith pursuant to the waiver of 37 C.F.R. § 1.98(a)(2)(iii) issued by the Office on Sep. 21, 2004.).

*Primary Examiner* — Venkataraman Balasubramanian
(74) *Attorney, Agent, or Firm* — Morrison & Foerster LLP

(57) ABSTRACT

The present invention relates to a novel method of preparing copanlisib, and copanlisib dihydrochloride, to novel intermediate compounds, and to the use of said novel intermediate compounds for the preparation of said copanlisib.

25 Claims, No Drawings

SYNTHESIS OF COPANLISIB AND ITS DIHYDROCHLORIDE SALT

CROSS REFERENCE TO RELATED APPLICATIONS

This application is the national stage of International Application No. PCT/EP2015/075765, filed internationally on Nov. 5, 2015, which claims the benefit of European Application No. 14192202.1, filed Nov. 7, 2014, the disclosures of which are hereby incorporated by reference in their entireties for all purposes.

FIELD OF THE INVENTION

The present invention relates to a novel method of preparing 2-amino-N-[7-methoxy-8-(3-morpholin-4-yl-propoxy)-2,3-dihydroimidazo-[1,2-c]quinazolin-5-yl]pyrimidine-5-carboxamide (7) and 2-amino-N-[7-methoxy-8-(3-morpholin-4-ylpropoxy)-2,3-dihydroimidazo-[1,2-c]quinazolin-5-yl]pyrimidine-5-carboxamide dihydrochloride (8), and to novel intermediate compounds, and to the use of said novel intermediate compounds for the preparation of said 2-amino-N-[7-methoxy-8-(3-morpholin-4-ylpropoxy)-2,3-dihydroimidazo-[1,2-c]quinazolin-5-yl]pyrimidine-5-carboxamide (7) and 2-amino-N-[7-methoxy-8-(3-morpholin-4-ylpropoxy)-2,3-dihydroimidazo-[1,2-c]quinazolin-5-yl]pyrimidine-5-carboxamide dihydrochloride (8):

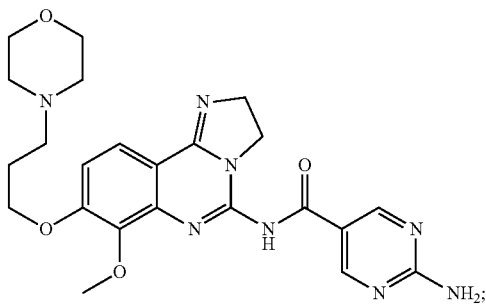

(7)

2-amino-N-[7-methoxy-8-
(3-morpholin-4-ylpropoxy)-2,3-dihydroimidazo-
-[1,2-c]quinazolin-5-yl]pyrimidine-5-carboxamide,
COPANLISIB,

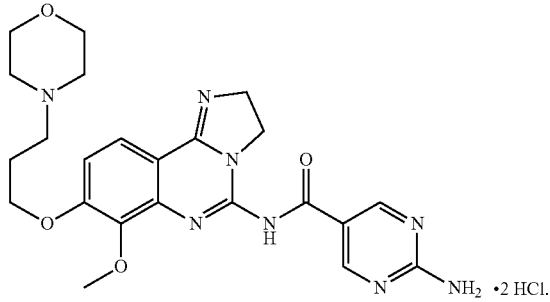

(8)

2-amino-N-[7-methoxy-8-
(3-morpholin-4-ylpropoxy)-2,3-dihydroimidazo-
-[1,2-c]quinazolin-5-yl]pyrimidine-5-carboxamide
dihydrochloride,

BACKGROUND TO THE INVENTION 2-amino-N-[7-methoxy-8-(3-morpholin-4-ylpropoxy)-2,3-dihydroimidazo[1,2-c]quinazolin-5-yl]pyrimidine-5-carboxamide (7), (which is hereinafter referred to as "copanlisib"), is a proprietary cancer agent with a novel mechanism of action, inhibiting Class I phosphatidylinositol-3-kinases (PI3Ks). This class of kinases is an attractive target since PI3Ks play a central role in the transduction of cellular signals from surface receptors for survival and proliferation. Copanlisib exhibits a broad spectrum of activity against tumours of multiple histologic types, both in vitro and in vivo.

Copanlisib may be synthesised according to the methods given in international patent application PCT/EP2003/010377, published as WO 04/029055 A1 on Apr. 8, 2004, (which is incorporated herein by reference in its entirety), on pp. 26 et seq.

Copanlisib is published in international patent application PCT/US2007/024985, published as WO 2008/070150 A1 on Jun. 12, 2008, (which is incorporated herein by reference in its entirety), as the compound of Example 13: 2-amino-N-[7-methoxy-8-(3-morpholin-4-ylpropoxy)-2,3-dihydroimidazo[1,2-c]quinazolin-5-yl]pyrimidine-5-carboxamide.

Copanlisib may be synthesized according to the methods given in WO 2008/070150, pp. 9 et seq., and on pp. 42 et seq. Biological test data for said compound of formula (I) is given in WO 2008/070150 on pp. 101 to 107.

2-amino-N-[7-methoxy-8-(3-morpholin-4-ylpropoxy)-2,3-dihydroimid-azo[1,2-c]quinazolin-5-yl]pyrimidine-5-carboxamide dihydrochloride (8), (which is hereinafter referred to as "copanlisib dihydrochloride") is published in international patent application PCT/EP2012/055600, published as WO 2012/136553 on Oct. 11, 2012, (which is incorporated herein by reference in its entirety), as the compound of Examples 1 and 2: 2-amino-N-[7-methoxy-8-(3-morpholin-4-ylpropoxy)-2,3-dihydroimidazo[1,2-c]quinazolin-5-yl]pyrimidine-5-carboxamide dihydrochloride: it may be synthesized according to the methods given in said Examples 1 and 2.

Copanlisib may exist in one or more tautomeric forms: tautomers, sometimes referred to as proton-shift tautomers, are two or more compounds that are related by the migration of a hydrogen atom accompanied by the migration of one or more single bonds and one or more adjacent double bonds.

Copanlisib may for example exist in tautomeric form (Ia), tautomeric form (Ib), or tautomeric form (Ic), or may exist as a mixture of any of these forms, as depicted below. It is intended that all such tautomeric forms are included within the scope of the present invention.

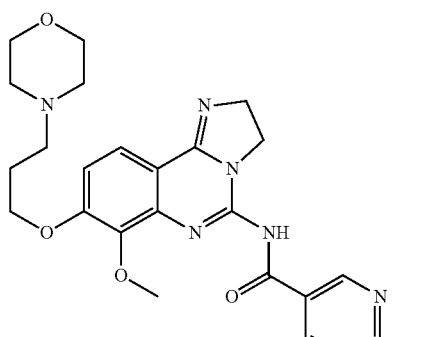

(Ia)

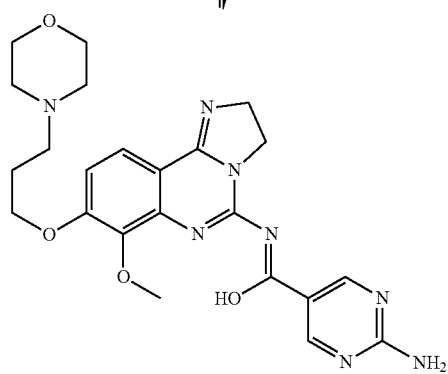

(Ib)

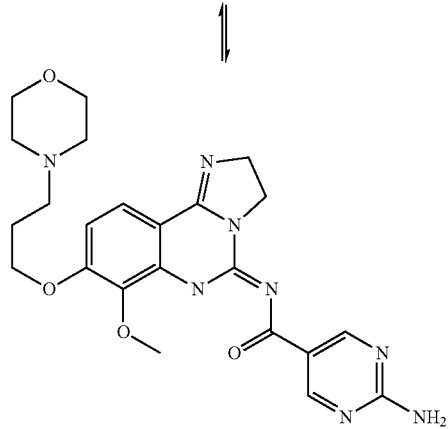

(Ic)

Copanlisib may exist as a solvate: a solvate for the purpose of this invention is a complex of a solvent and copanlisib in the solid state. Exemplary solvates include, but are not limited to, complexes of copanlisib with ethanol or methanol.

Copanlisib may exist as a hydrate: Hydrates are a specific form of solvate wherein the solvent is water.

As mentioned supra, copanlisib is, in WO 2008/070150, described on pp. 9 et seq., and may be synthesized according to the methods given therein on pp. 42 et seq., viz.:

Reaction Scheme 1:

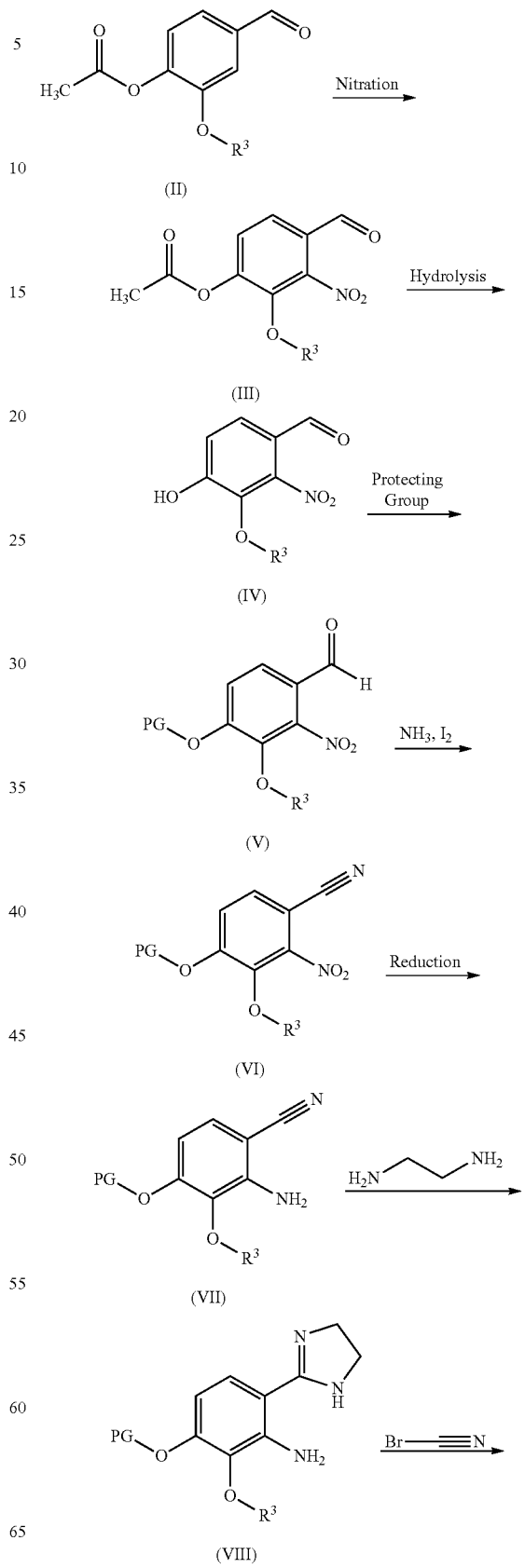

-continued

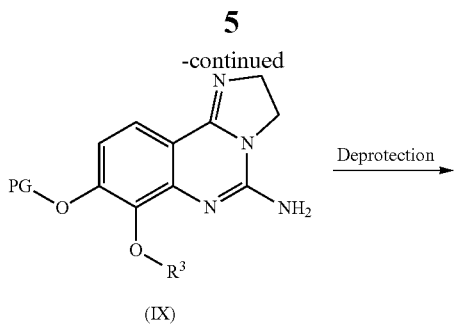

(IX)

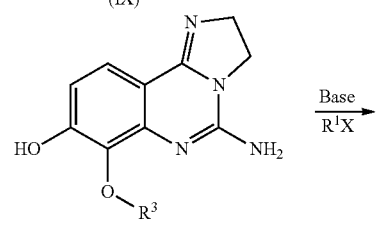

(X)

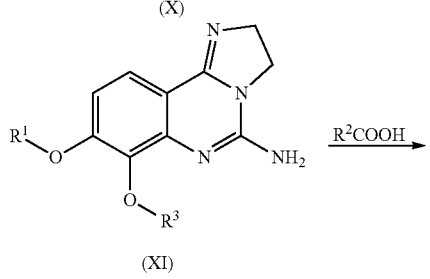

(XI)

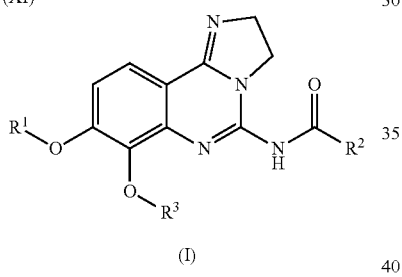

(I)

In Reaction Scheme 1, vanillin acetate can be converted to intermediate (III) via nitration conditions such as neat fuming nitric acid or nitric acid in the presence of another strong acid such as sulfuric acid. Hydrolysis of the acetate in intermediate (III) would be expected in the presence of bases such as sodium hydroxide, lithium hydroxide, or potassium hydroxide in a protic solvent such as methanol. Protection of intermediate (IV) to generate compounds of Formula (V) could be accomplished by standard methods (Greene, T. W.; Wuts, P. G. M.; *Protective Groups in Organic Synthesis*; Wiley & Sons: New York, 1999). Conversion of compounds of formula (V) to those of formula (VI) can be achieved using ammonia in the presence of iodine in an aprotic solvent such as THF or dioxane. Reduction of the nitro group in formula (VI) could be accomplished using iron in acetic acid or hydrogen gas in the presence of a suitable palladium, platinum or nickel catalyst. Conversion of compounds of formula (VII) to the imidazoline of formula (VIII) is best accomplished using ethylenediamine in the presence of a catalyst such as elemental sulfur with heating. The cyclization of compounds of formula (VIII) to those of formula (IX) is accomplished using cyanogen bromide in the presence of an amine base such as triethylamine, diisopropylethylamine, or pyridine in a halogenated solvent such as DCM or dichloroethane. Removal of the protecting group in formula (IX) will be dependent on the group selected and can be accomplished by standard methods (Greene, T. W.; Wuts, P. G. M.; *Protective Groups in Organic Synthesis*; Wiley & Sons: New York, 1999). Alkylation of the phenol in formula (X) can be achieved using a base such as cesium carbonate, sodium hydride, or potassium t-butoxide in a polar aprotic solvent such as DMF or DMSO with introduction of a side chain bearing an appropriate leaving group such as a halide, or a sulfonate group. Lastly, amides of formula (I) can be formed using activated esters such as acid chlorides and anhydrides or alternatively formed using carboxylic acids and appropriate coupling agents such as PYBOP, DCC, or EDCI in polar aprotic solvents.

Reaction Scheme 2:

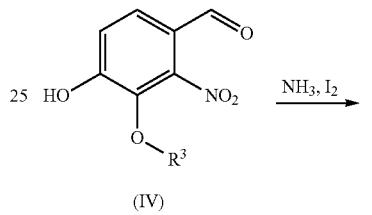

(IV)

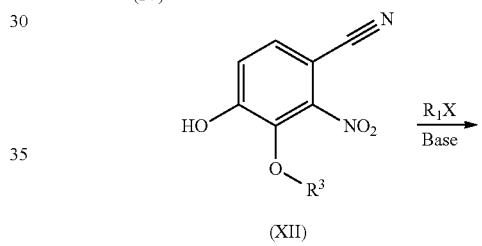

(XII)

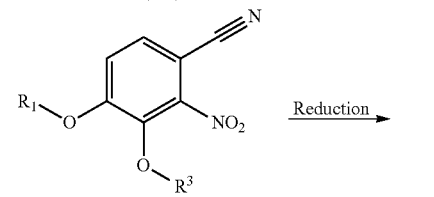

(XIII)

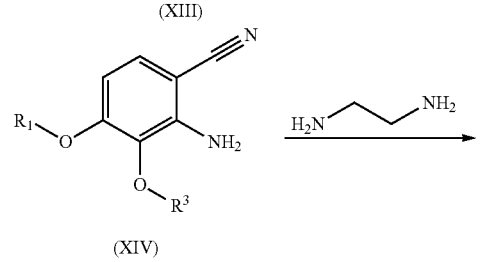

(XIV)

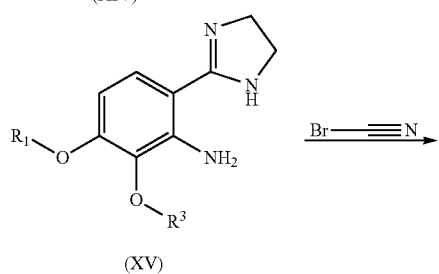

(XV)

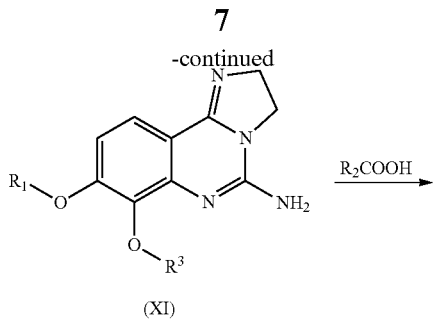

(XI)

R₂COOH →

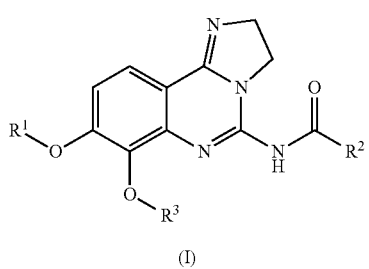

(I)

In Reaction Scheme 2, a compound of formula (IV), prepared as described above, can be converted to a structure of formula (XII) using ammonia in the presence of iodine in an aprotic solvent such as THF or dioxane. Alkylation of the phenol in formula (XII) can be achieved using a base such as cesium carbonate, sodium hydride, or potassium t-butoxide in a polar aprotic solvent such as DMF or DMSO with introduction of a side chain bearing an appropriate leaving group such as a halide, or a sulfonate group. Reduction of the nitro group in formula (XIII) could be accomplished using iron in acetic acid or hydrogen gas in the presence of a suitable palladium, platinum or nickel catalyst. Conversion of compounds of formula (XIV) to the imidazoline of formula (XV) is best accomplished using ethylenediamine in the presence of a catalyst such as elemental sulfur with heating. The cyclization of compounds of formula (XV) to those of formula (XVI) is accomplished using cyanogen bromide in the presence of an amine base such as triethylamine, diisopropylethylamine, or pyridine in a halogenated solvent such as DCM or dichloroethane. Lastly, amides of formula (I) can be formed using activated esters such as acid chlorides and anhydrides or alternatively formed using carboxylic acids and appropriate coupling agents such as PYBOP, DCC, or EDCI in polar aprotic solvents.

The two already known synthetic pathways, Reaction Schemes 1 and 2, supra, suffer from numerous disadvantages which pose especially problems at larger scale:

- Batchwise nitration of a molecule which is susceptible to oxidation is problematic for scale-up due to safety-concerns. For this reason, we developed a continuous process via microreaction-technology, as exemplified in Example 1 (vide infra).
- Conversion of the aldehyde-group into a nitrile with ammonia and iodine as reagents is dangerous as ammonia and iodine may form nitrogen triiodide, a highly sensitive explosive substance.
- The cyclisation with ethylenediamine to the imidazoline-ring needs sulfur. As sulfur is very difficult in cleaning processes in technical systems with fixed reactors and tubings, this cyclisation reaction is not suitable for scaleup.
- Reduction of the nitro group to the corresponding amine on larger scale is difficult with iron and acid. Standard catalytic reductions often suffer from side reactions, e.g. imidazoline ring-opening which reduces the yield significantly.

It was therefore desirable to devise a new synthesis, which circumvents these disadvantages and is suitable for production scale/industrial scale.

It has been very surprisingly discovered, and this provides the basis of the present invention, that compounds of the following structure-type, in particular copanlisib, can be synthesized according to the following scheme, see Reaction Scheme 3, infra:

Reaction Scheme 3:

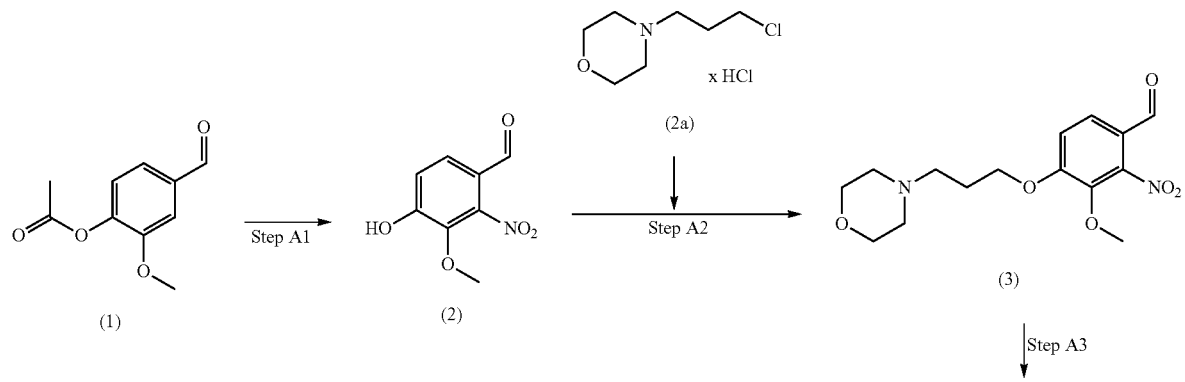

-continued

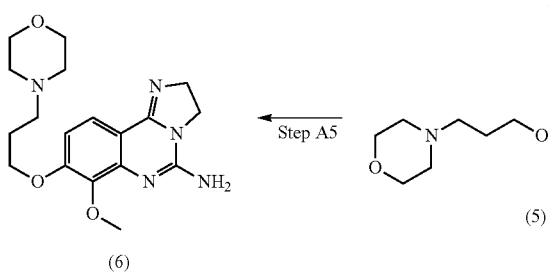

(6)

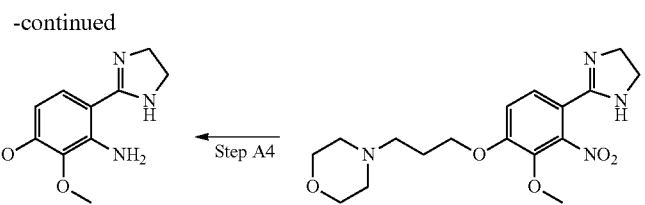

(5) ← Step A4 — (4)

← Step A5

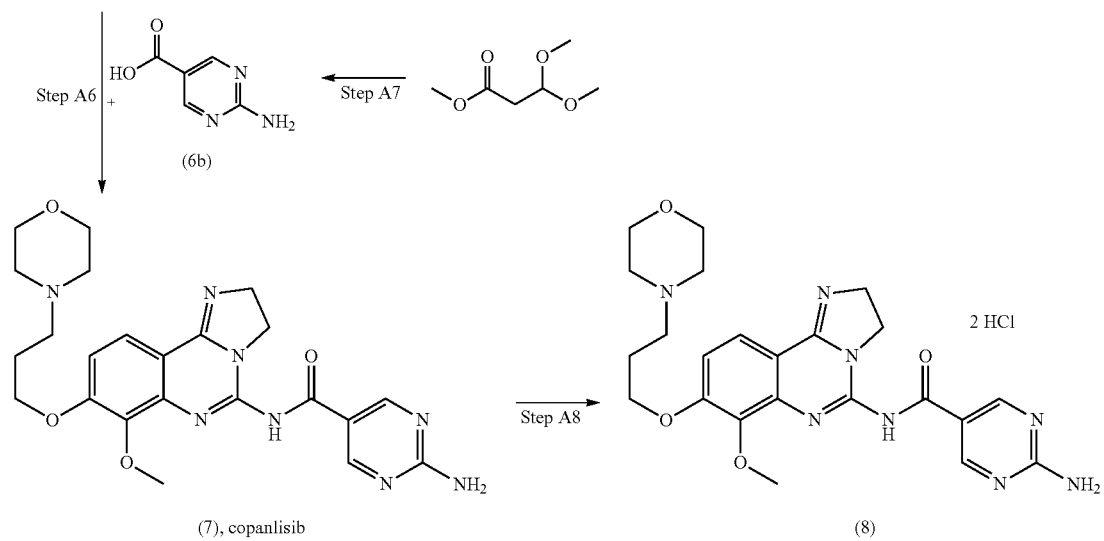

(7), copanlisib

Step A8 →

(8) · 2 HCl

First of all, the synthesis of the present invention, as depicted in Reaction Scheme 3, supra, does not need any protection chemistry which in general reduces the number of chemical steps needed at least by 2 steps (protection and deprotection). Of course, if needed or wanted, many sorts of protection chemistry are compatible with the new synthesis (Greene, T. W.; Wuts, P. G. M.; *Protective Groups in Organic Synthesis*; Wiley & Sons: New York, 1999).

More particularly, the following further advantages of the specific steps of the synthesis of the present invention, as depicted in Reaction Scheme 3, supra, are given infra:

Step A1: The nitration reaction is performed in a microreactor system, thereby the exothermic reaction is easily controlled and no danger of a runaway reaction is given. Kilogramme-quantities of 2-nitrovanillin can easily be prepared within days or a few weeks. The isolated material contains the undesired regioisomer 6-nitrovanillin in similar amounts as material produced by the batch nitration.

Step A2: Simple alkylation mediated by a base like potassium carbonate, high yield.

Step A3: Direct conversion of the aldehyde to the imidazoline in a one-pot reaction of cyclisation and oxidation with ethylenediamine and N-bromosuccinimide (abbreviated herein to "NBS"). This new sequence solves two issues, as it circumvents:
a) the use of ammonia/iodine for the conversion of the aldehyde to the nitrile (safety concerns), and
b) the use of sulfur during the imidazoline synthesis (scale-up issue).

Step A3 has no safety issues, and is easily scaleable.

Step A4: Reduction with hydrogen and a specially prepared catalyst. It consists of palladium and iron on charcoal. Elemental iron is essential, side-reactions are suppressed.

Step A5: No changes to the reagent. Crystallization of the crude product with e.g. isopropanol improves the quality of the isolated product significantly (compared to synthetic procedure described in WO 2008/070150 page 85) by removing by-product triethylamine hydrobromide.

Step A6: N-[3-(dimethylamino)propyl]-N'-ethylcarbodiimide hydrochloride (abbreviated herein to "EDCI") is used as coupling reagent.

Step A7: Advantages compared to synthesis described in WO 2008/070150 (page 59, intermediate B): substitution of sodium hydride with sodium methoxide for the reaction of methyl 3,3-dimethoxypropanoate with methyl formate, one-pot procedure from methyl 3,3-dimethoxypropanoate to crude 2-aminopyrimidin-5-carboxylic acid, therefore no need to isolate hygroscopic intermediate 3,3-dimethoxy-2-methoxycarbonylpropen-1-ol sodium salt, and easy purification of crude 2-aminopyrimidine-5-carboxylic acid via the dicyclohexylamine salt.

Step A8: Easy purification of copanlisib via dihydrochloride (dihydrochloride is the final product).

Hence, in a first aspect, the present invention relates to a method of preparing copanlisib (7) via the following steps shown in Reaction Scheme 3, infra:

Reaction Scheme 3:
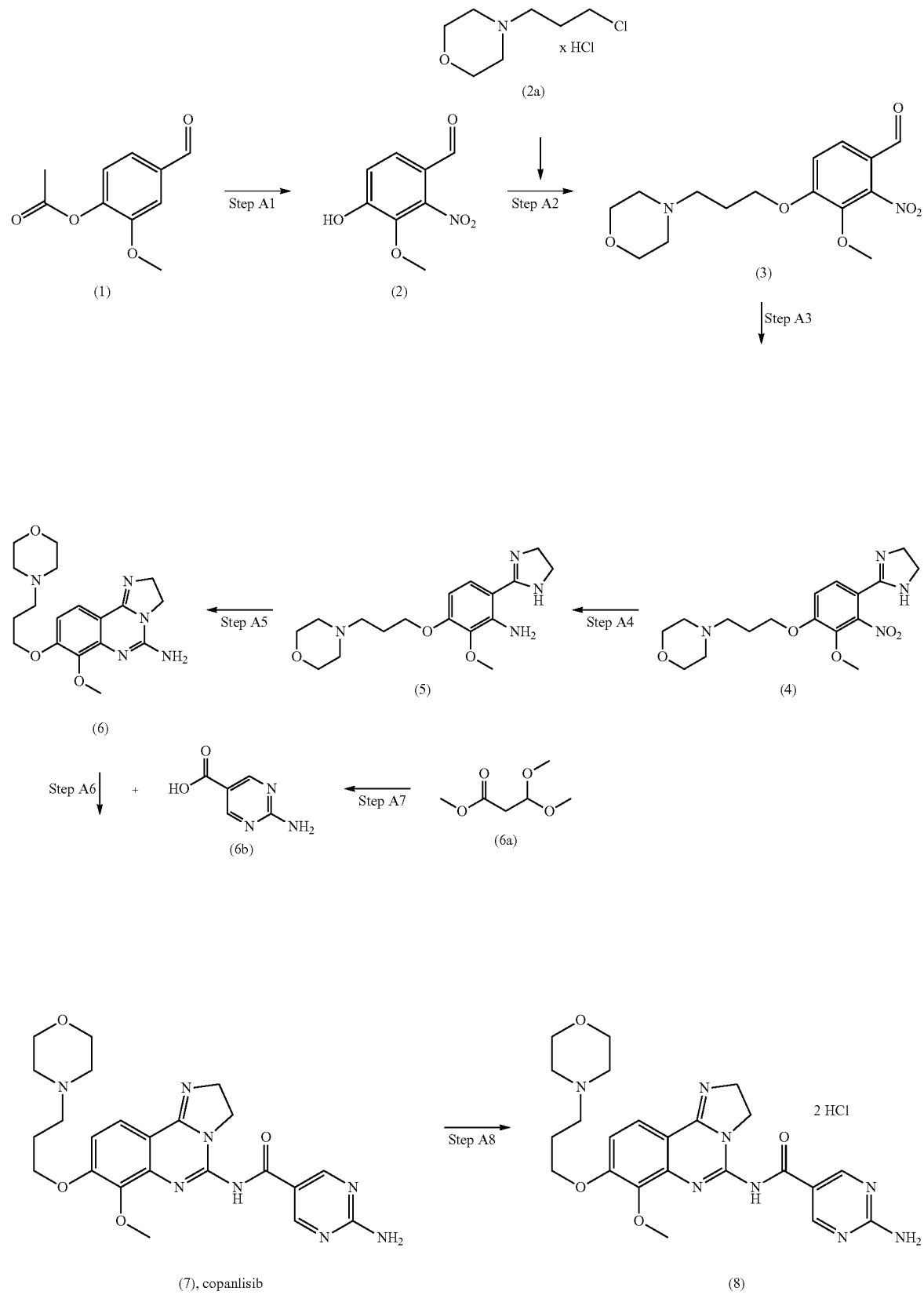

In an embodiment of the first aspect, the present invention relates to a method of preparing copanlisib (7)

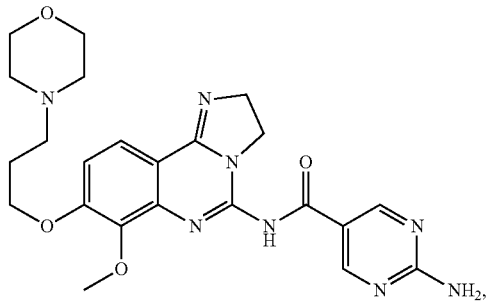

comprising the following steps:
step A6:
wherein a compound of formula (6):

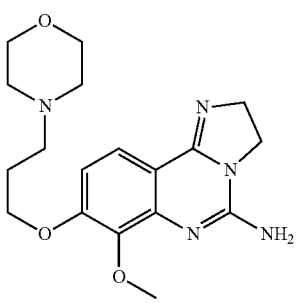

is allowed to react with a compound of formula (6b):

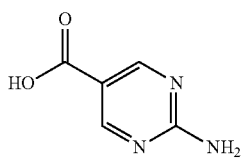

optionally in the presence of a catalyst, such as N,N-dimethyl-4-aminopyridine for example, optionally in the presence of a coupling agent, such as N-[3-(dimethylamino)propyl]-N'-ethylcarbodiimide hydrochloride for example, optionally in a solvent, such as N,N-dimethylformamide for example, thereby providing copanlisib (7):

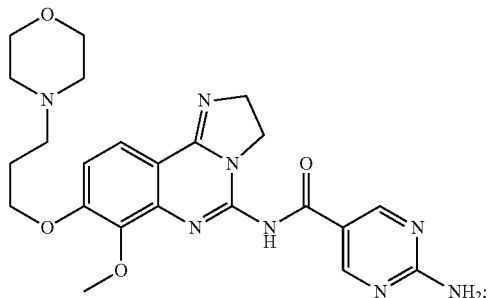

said compound of formula (6):

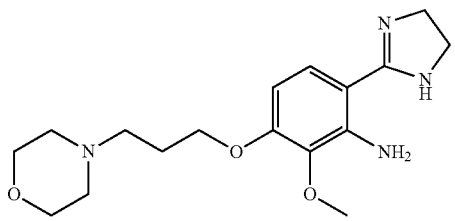

being prepared by the following step A5:
wherein a compound of formula (5):

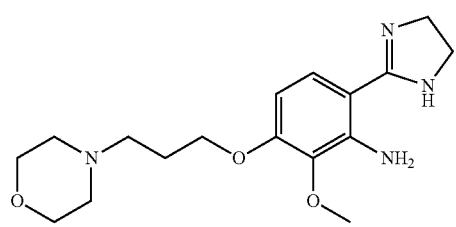

is allowed to react, optionally in the presence of a base, such as triethylamine for example, with an annelating agent, such as cyanogen bromide for example, be optionally in a solvent, such as dichloromethane for example, thereby providing a compound of formula (6);
said compound of formula (5):

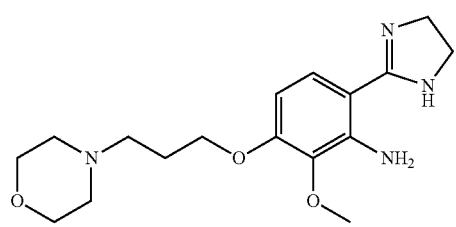

being prepared by the following step A4:
wherein a compound of formula (4):

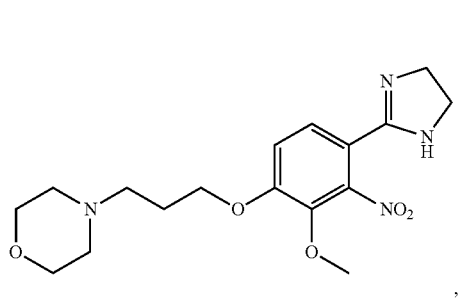

(4)

is allowed to react with hydrogen in the presence of a 5% palladium/1% iron catalyst on carbon which is water-wetted, in a solvent, such as methanol for example, thereby providing a compound of formula (5),
said copanlisib of formula (7):

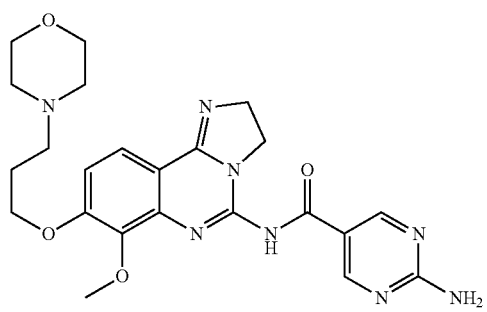

(7)

being optionally to copanlisib dihydrochloride (8) by being allowed to react with hydrogen chloride, optionally hydrochloric acid,
thereby providing copanlisib dihydrochloride (8):

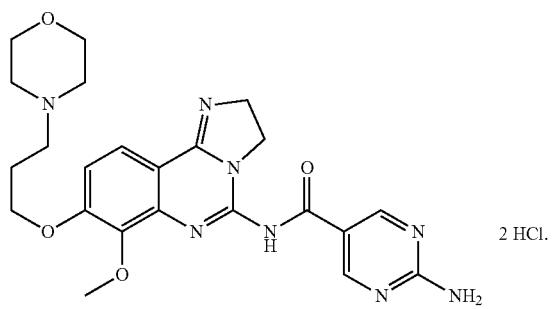

(8)

In an embodiment of the first aspect, the present invention relates to a method of preparing copanlisib dihydrochloride (8):

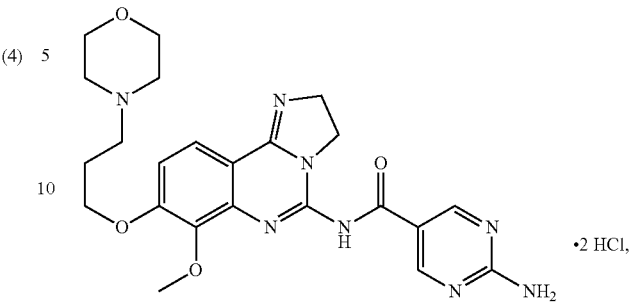

·2 HCl, (8)

comprising the following step A8:
wherein copanlisib, of formula (7):

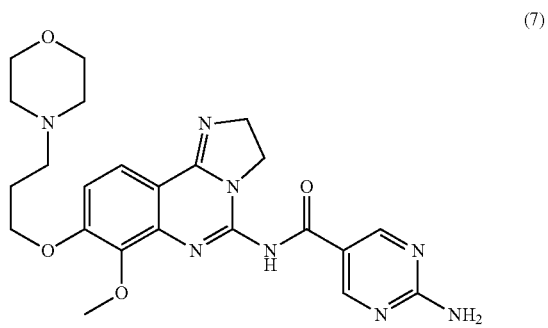 [SMILES: COc1c(OCCCN2CCOCC2)ccc2c1N=C(NC(=O)c1cnc(N)nc1)N1CCN=C21]

(7)

is allowed to react with hydrogen chloride, optionally hydrochloric acid,
thereby providing copanlisib dihydrochloride (8):

(8)

2 HCl.

In an embodiment of the first aspect, the present invention relates to a method of preparing copanlisib (7):

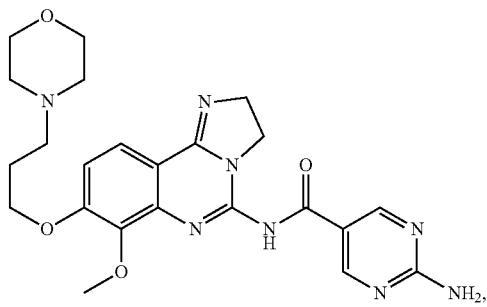

comprising the following step A6:
wherein a compound of formula (6):

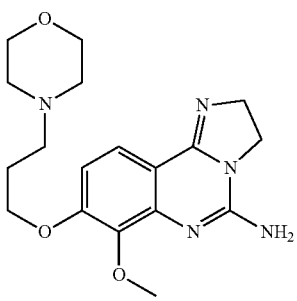

is allowed to react with a compound of formula (6b):

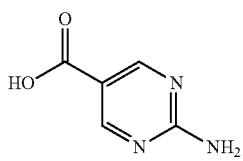

optionally in the presence of a catalyst, such as N,N-dimethyl-4-aminopyridine for example, optionally in the presence of a coupling agent, such as N-[3-(dimethylamino)propyl]-N'-ethylcarbodiimide hydrochloride for example, optionally in a solvent, such as N,N-dimethylformamide for example, thereby providing copanlisib (7):

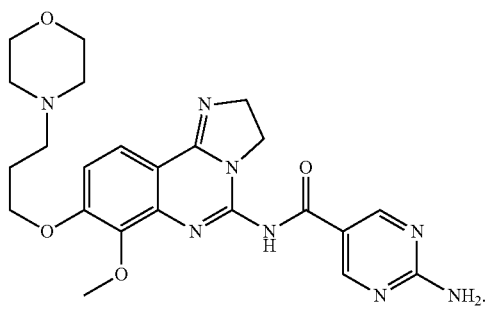

In a further embodiment of the first aspect of the present invention, the above-mentioned compound of formula (6b):

is prepared by the following step A7:
wherein a compound of formula (6a):

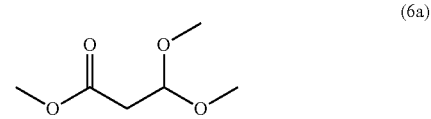

is:
a) allowed to react with a base, such as sodium methoxide for example, optionally in a solvent, such as 1,4-dioxane for example, with heating, such as under reflux for example, then,
b) after cooling, such as to room temperature for example, adding methyl formate, then
c) adding guanidine hydrochloride, followed by heating, such as under reflux for example, then,
d) adding water and an aqueous solution of a base, such as sodium hydroxide for example, followed by heating, then,
e) adding an aqueous solution of a mineral acid, such as hydrochloric acid for example,
f) adding an amine, such as dicyclohexylamine for example, and filter, then
g) adding an aqueous solution of a strong base, such as sodium hydroxide, then
h) adding an aqueous solution of a mineral acid, such as hydrochloric acid for example
thereby providing a compound of formula (6b):

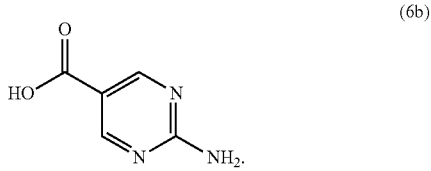

In a further embodiment of the first aspect of the present invention, the above-mentioned compound of formula (6):

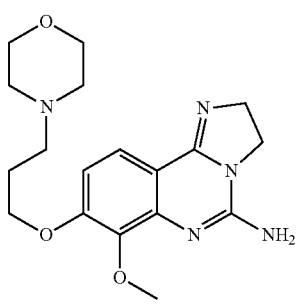

is prepared by the following step A5:
wherein a compound of formula (5):

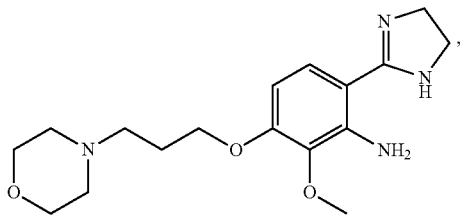
(5)

is allowed to react, optionally in the presence of a base, such as triethylamine for example, with an annelating agent, such as cyanogen bromide for example, optionally in a solvent, such as dichloromethane for example, thereby providing a compound of formula (6).

In a further embodiment of the first aspect of the present invention, the above-mentioned compound of formula (5):

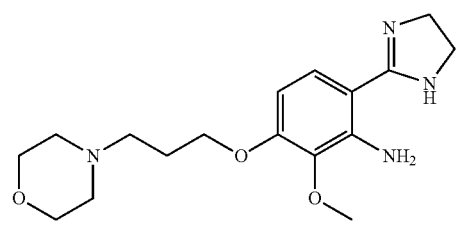
(5)

is prepared by the following step A4:
wherein a compound of formula (4):

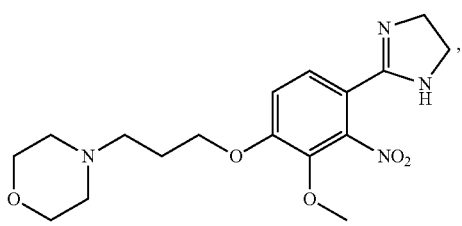
(4)

is allowed to react with a reducing agent, such as hydrogen for example, optionally in the presence of a catalyst, such as a bimetallic catalyst such as palladium/iron on carbon for example, particularly 5% palladium/1% iron on carbon which is water-wetted, optionally dissolved in a solvent or in suspension in a solvent, such as methanol for example, thereby providing a compound of formula (5).

In a particular embodiment of the first aspect of the present invention, the above-mentioned compound of formula (5):

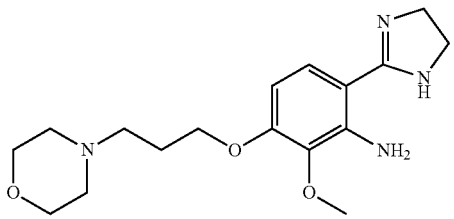
(5)

is prepared by the following step A4:
wherein a compound of formula (4):

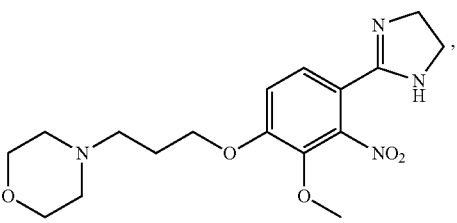
(4)

is allowed to react with hydrogen in the presence of a 5% palladium/1% iron catalyst on carbon which is water-wetted, in suspension in a solvent, such as methanol for example, thereby providing a compound of formula (5).

In a further embodiment of the first aspect of the present invention, the above-mentioned compound of formula (4):

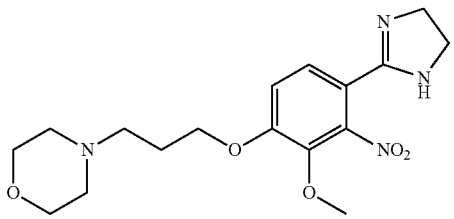
(4)

is prepared by the following step A3:
wherein a compound of formula (3):

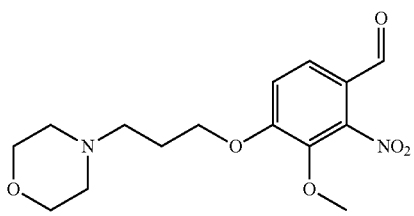
(3)

is allowed to react with ethylenediamine, optionally in the presence of N-bromosuccinimide, optionally in a solvent, such as dichloromethane for example, thereby providing a compound of formula (4).

In a further embodiment of the first aspect of the present invention, the above-mentioned compound of formula (3):

wherein a compound of formula (1):

(1)

[Structure of compound (1): 4-formyl-2-methoxyphenyl acetate]

a) optionally in solution in a solvent, such as dichloromethane for example, is allowed to react with nitric acid and sulphuric acid, and then
b) adding a base, such as potassium carbonate for example, optionally in a solvent, such as methanol for example, thereby providing a compound of formula (2).

In a further embodiment of the first aspect, the present invention relates to a method of preparing copanlisib (7), wherein each of said steps A1, A2, A3, A4, A5, A6 and A7 as shown in Scheme 3, supra, are described supra.

In accordance with a second aspect, the present invention relates to intermediate compounds which are useful in the preparation of copanlisib (7) and copanlisib dihydrochloride (8).

In an embodiment of said second aspect, the present invention relates to a compound:

(6)

[Structure of compound (6)]

In an embodiment of said second aspect, the present invention relates to a compound:

(6b)

[Structure of compound (6b): 2-aminopyrimidine-5-carboxylic acid]

In an embodiment of said second aspect, the present invention relates to a compound:

(6a)

[Structure of compound (6a)]

In an embodiment of said second aspect, the present invention relates to a compound:

(3)

[Structure of compound (3)]

is prepared by the following step A2:
wherein a compound of formula (2):

(2)

[Structure of compound (2)]

optionally in a solvent, such as acetonitrile for example, optionally in the presence of a base, such as potassium carbonate for example,
is allowed to react with a compound of formula (2a):

(2a)

[Structure of compound (2a): 4-(3-chloropropyl)morpholine hydrochloride]
x HCl optionally in a solvent, such as acetonitrile for example, optionally with heating, such as under reflux for example,
thereby providing a compound of formula (3).

In a further embodiment of the first aspect of the present invention, the above-mentioned compound of formula (2):

(2)

[Structure of compound (2)]

is prepared by the following step A1

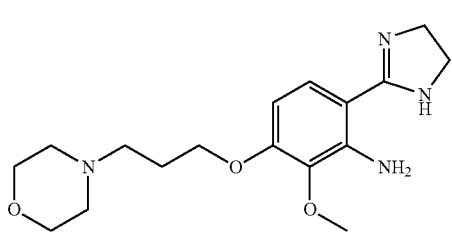
(5)

In an embodiment of said second aspect, the present invention relates to a compound:

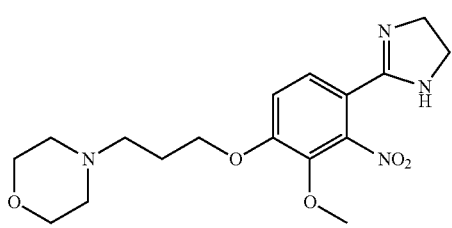
(4)

In an embodiment of said second aspect, the present invention relates to a compound:

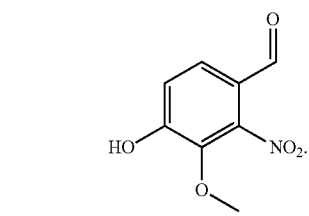
(3)

In an embodiment of said second aspect, the present invention relates to a compound:

(2)

HO — NO₂
    |
    O—

In an embodiment of said second aspect, the present invention relates to a compound:

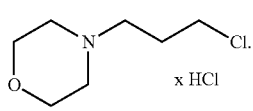
(2a)

x HCl

In an embodiment of said second aspect, the present invention relates to a compound:

(1)

In accordance with a third aspect, the present invention relates to the use of the intermediate compounds of said second aspect for preparing copanlisib (7) and copanlisib hydrochloride (8).

In an embodiment of third second aspect, the present invention relates to the use of:

(6)

for preparing copanlisib (7) or copanlisib hydrochloride (8).

In an embodiment of third second aspect, the present invention relates to the use of:

(6b)

for preparing copanlisib (7) or copanlisib hydrochloride (8).

In an embodiment of said third aspect, the present invention relates to the use of:

(6a)

for preparing copanlisib (7) or copanlisib hydrochloride (8).

In an embodiment of said third aspect, the present invention relates to the use of:

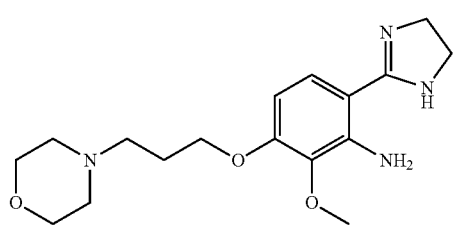

(5)

for preparing copanlisib (7) or copanlisib hydrochloride (8).

In an embodiment of said third aspect, the present invention relates to the use of:

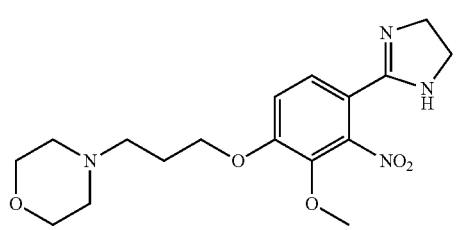

(4)

for preparing copanlisib (7) or copanlisib hydrochloride (8).

In an embodiment of said third aspect, the present invention relates to the use of:

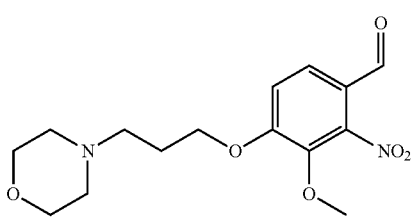

(3)

for preparing copanlisib (7) or copanlisib hydrochloride (8).

In an embodiment of said third aspect, the present invention relates to the use of:

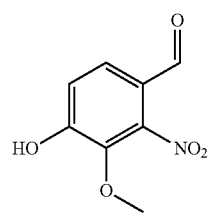

(2)

for preparing copanlisib (7) or copanlisib hydrochloride (8).

In an embodiment of said third aspect, the present invention relates to the use of:

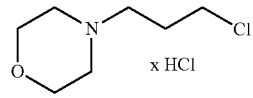

(2a)

for preparing copanlisib (7) or copanlisib hydrochloride (8).

In an embodiment of said third aspect, the present invention relates to a compound

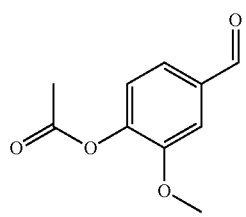

(1)

for preparing copanlisib (7) or copanlisib hydrochloride (8).

Within the context of the present invention the term "solvent", as optionally present in any reaction step of the method of the invention, is understood, as is by the person skilled in the art, as meaning any substance in which other materials dissolve to form a solution, such as, without being limited to: a polar solvent, such as a polar protic solvent, such as water, n-butanol, isopropanol, n-propanol, ethanol, methanol, or formic acid or acetic acid, etc., for example; a polar aprotic solvent, such as 1,4-dioxane, tetrahydrofuran, 1,2-dimethoxyethane, acetone, acetonitrile, dimethylformamide, sulfolane, pyridine or dimethylsulphoxide, etc., for example; or a non-polar solvents, such as pentane, hexane, benzene, toluene, diethyl ether, methyl ethyl ketone, dichloromethane, chloroform, tetrachloromethane, ethyl acetate, etc., for example; or any mixture of the solvents listed above.

It is understood that any combination of the definitions given in the above-mentioned embodiments is possible within the context of the present invention.

The invention will be better understood upon reading the Examples below, which are provided as an illustration of the present invention. The Examples below in no way whatsoever constitute a limitation of the present invention as described in the present text and as defined in the claims appended hereto.

EXPERIMENTAL SECTION

Abbreviations Used:
The following abbreviations used in the Examples have the following meanings:
1H-NMR proton nuclear magnetic resonance spectroscopy (chemical shifts (δ) are given in ppm)
Ac acetyl
Boc tert-butyloxycarbonyl
bm broad multiplet
br broad
bs broad singlet
c- cyclo-
d doublet
dd doublet of doublets
DCM dichloromethane
DME 1,2-dimethoxyethane
DIPE diisopropylether DIPEA N,N-diisopropylethylamine
DMF N,N-dimethylformamide
DMSO dimethyl sulfoxide
EDCI N-[3-(dimethylamino)propyl]-N'-ethylcarbodiimide hydrochloride
Eq equivalent
ESI electrospray ionisation
HATU N-[(dimethylamino)(3H-[1,2,3]triazolo[4,5-b]pyridin-3-yloxy)-methylene]-N-methylmethanaminium hexafluorophosphate
Hünig Base N,N-diisopropylethylamine
m multiplet
m.p. melting point in ° C
MS mass spectrometry
MW molecular weight
NaOtBu sodium tert-butoxide; sodium 2-methylpropan-2-olate
NMP N-methylpyrrolidinone
NMR nuclear magnetic resonance spectroscopy: chemical shifts (δ) are given in ppm.
q quartet
quin quintett
Rac racemic
Rt room temperature
r.t. room temperature
RT retention time in minutes
s singlet
t triplet
TBAF tetrabutylammoniumfluoride
TBTU N-[(1H-benzotriazol-1-yloxy)(dimethylamino)methylene]-N-methylmethanaminium tetrafluoroborate
TEA triethylamine
TFA trifluoroacetic acid
THF tetrahydrofuran
TMS trimethylsilyl
Ts para toluenesulfonyl; (tosyl)
UPLC ultra performance liquid chromatography

EXAMPLES

Example 1

Step A1: Preparation of 4-hydroxy-3-methoxy-2-nitrobenzaldehyde (2-nitro-vanillin) (2)

2-Nitrovanilin (2) was synthesized via a flow nitration of vanillin acetate (1) in a micro reactor. 3.94 kg of nitric acid (65 w %) were added to 5.87 kg of concentrated sulfuric acid at 0° C. (nitrating acid). 1.5 kg of vanillin acetate were dissolved in 2.9 kg of dichloromethane (vanillin acetate solution). Both solutions reacted in a micro reactor with flow rates of app. 8.0 mL/min (nitrating acid) and app. 4.0 mL/min (vanillin acetate solution) at 5° C. The reaction mixture was directly dosed into 8 kg of water at 3° C. After 3 h flow rates were increased to 10 mL/min (nitrating acid) and 5.0 mL/min (vanillin acetate solution). After additional 9 h the flow reaction was completed. The layers were separated at r.t., and the aqueous phase was extracted with 2 L of dichloromethane. The combined organic phases were washed with 2 L of saturated sodium bicarbonate, and then 0.8 L of water. The dichloromethane solution was concentrated in vacuum to app. 3 L, 3.9 L of methanol were added and app. the same volume was removed by distillation again. Additional 3.9 L of methanol were added, and the solution concentrated to a volume of app. 3.5 L. 1.25 kg of methanol were added, followed by 2.26 kg of potassium carbonate. The mixture was stirred at 30° C. for 3 h. 7.3 kg of dichloromethane and 12.8 kg of aqueous hydrochloric acid (10 w %) were added at <30° C. (pH 0.5-1). The mixture was stirred for 15 min, and the layers were separated. The organic layer was filtered, and the filter cake washed with 0.5 L of dichloromethane. The aqueous layer was extracted twice with 4.1 kg of dichloromethane. The combined organic layers were concentrated in vacuum to app. 4 L. 3.41 kg of toluene were added, and the mixture concentrated to a final volume of app. 4 L. The mixture was cooled to 0° C. After 90 min the suspension was filtered. The collected solids were washed with cold toluene and dried to give 0.95 kg (62%).

$^1$H-NMR (400 MHz, $d_6$-DMSO): δ=3.84 (s, 3H), 7.23 (d, 1H), 7.73 (d, 1H), 9.74 (s, 1H), 11.82 (brs, 1H).

NMR spectrum also contains signals of regioisomer 6-nitrovanillin (app. 10%): δ=3.95 (s, 3H), 7.37 (s, 1H), 7.51 (s, 1H), 10.16 (s, 1H), 11.11 (brs, 1H).

Example 2

Step A2: Preparation of 3-methoxy-4-[3-(morpholin-4-yl)propoxy]-2-nitrobenzaldehyde (3)

854 g of 4-(3-chloropropyl)morpholine hydrochloride were suspended in 19.4 L of acetonitrile and the mixture was stirred for 50 min. at r.t. The mixture was filtered, and the residue was washed with 0.7 L of acetonitrile. The filtrate was dosed to a suspension of 700 g of 2-nitrovanilline and 1.96 kg of potassium carbonate in 7 L of acetonitrile at r.t. over a period of ca. 2 h. The reaction mixture was heated to reflux, and stirred at reflux for 3 h. The mixture was cooled to r.t., and filtered. The residue was washed twice with acetonitrile. The filtrate was concentrated under vacuum and the residue dissolved in 5.6 L of ethyl acetate. This solution is washed with 7 L of aqueous 10 w % sodium chloride solution, then 7.7 L of aqueous 1% sodium chloride solution. After removal of the solvent, the viscous residue of ca. 1.14 kg was dissolved in 2.3 L of dichloromethane, the solvent of the next step.

$^1$H-NMR (500 MHz, $d_6$-DMSO): d=1.97 (m, 2H); 2.36 (m, 4 H); 2.45 (t, 2H); 3.56 (m, 4H); 3.85 (s, 3H); 4.27 (t, 2H); 7.51 (d, 1H); 7.87 (d, 1H); 9.80 (s, 1H).

Example 3

Step A3: Preparation of 4-{3-[4-(4,5-dihydro-1H-imidazol-2-yl)-2-methoxy-3-nitrophenoxy]propyl}morpholine (4)

6.1 kg of the dichoromethane solution from the previous reaction (containing 5.25 mol of 3-methoxy-4-[3-(morpholin-4-yl)propoxy]-2-nitrobenzaldehyde; example 2) was diluted with 25.7 L of dichloromethane. Over a period of 10 min. 836 g of ethylenediamine were added, and the reaction mixture was stirred for 1 h at r.t. After cooling to 0° C., 2.476 kg of N-bromosuccinimide were added in three portions. The reaction mixture was warmed to 25° C. within 30 m in. and then cooled again to 0° C. The reaction mixture was stirred at 0° C. for 10 5 min. 2.3 L of saturated aqueous sodium bicarbonate solution were added, followed by 5.4 L of aqueous sodium hydroxide solution (20 w %) to adjust the solution to pH 14. 5.8 L of water were added, and the mixture was warmed to r.t. The organic phase was separated, washed with 12.9 L of water and dried over 1 kg of sodium sulfate. The filtrate was evaporated (1.87 kg residue).

This residue was combined with a second batch (1.83 kg), and suspended in 16 L of acetone. 13 L of n-heptane were added at r.t. within 30 min. The mixture was stirred at r.t. for 1 h, then cooled to 0° C. and stirred for 2 h at 0° C. The suspension was filtered. The collected solids were washed with n-heptane and dried to yield 2.9 kg (76%).

$^1$H-NMR (400 MHz, d$_6$-DMSO): δ=1.94 (m, 2H); 2.37 (bs, 4 H); 2.45 (t, 2H); 3.52 (m, 4H); 3.57 (m, 4H); 3.82 (s, 3H); 4.18 (t, 2H); 7.07 (bs, 1H); 7.33 (d, 1H); 7.48 (d, 1H).

Example 4

Step A4: Preparation of 6-(4,5-dihydro-1H-imidazol-2-yl)-2-methoxy-3-[3-(morpholin-4-yl)propoxy]aniline (5)

A mixture of 625 g of 4-{3-[4-(4,5-dihydro-1H-imidazol-2-yl)-2-methoxy-3-nitrophenoxy]propyl}morpholine (4) in 5 kg of methanol (saturated with potassium carbonate) and 63 g of catalyst (5% Pd/1% Fe on carbon, water-wetted) was stirred for 24 h under 100 bar hydrogen pressure at 40° C. The catalyst is filtered off under inert gas atmosphere, and washed with methanol to yield 6.1 kg of product solution. For work-up several batches of product solutions were combined. The solvent was switched to toluene by distillation in vacuum. The toluene product solution was filtered at 75° C., and then concentrated in vacuum until the product precipitates. The mixture was filtered, the solids washed with cold toluene and dried. Hydrogenation of 5 kg of 4-{3-[4-(4,5-dihydro-1H-imidazol-2-yl)-2-methoxy-3-nitrophenoxy]propyl}-morpholine (4) yielded 3.3 kg (71%).

$^1$H-NMR (400 MHz, d$_6$-DMSO): δ=1.88 (m, 2H); 2.36 (bs, 4 H); 2.44 (t, 2H); 3.26 (t, 2H); 3.57 (m, 4H); 3.66 (s, 3H); 3.82 (t, 2H); 4.02 (t, 2H); 6.25 (d, 1H); 6.70 (s, 1H); 6.90 (bs, 2H), 7.16 (d, 1H).

Example 5

Step A5: Preparation of 7-methoxy-8-[3-(morpholin-4-yl)propoxy]-2,3-dihydroimidazo[1,2-c]quinazolin-5-amine (6)

375 ml of triethylamine were added to 300 g of 6-(4,5-dihydro-1H-imidazol-2-yl)-2-methoxy-3-[3-(morpholin-4-yl)propoxy]aniline (5) in 3 L of dichloromethane. The solution was cooled to 0° C., and a solution of 98 g of bromocyanide in 300 mL of dichloromethane was added within ap. 0.5 h. The resulting suspension was stirred for 1 h at −5 to 0° C., and then 2 h at 10° C. The reaction mixture was washed three times with 675 mL saturated aqueous sodium bicarbonate solution. The organic phase was concentrated in vacuum. 1.1 L of isopropanol was added and the mixture was heated to ap. 75° C. ° C. The resulting solution was cooled to r.t. overnight, and then cooled to 5° C. and stirred for 2 h. The product was filtered off, washed twice with cold isopropanol, and dried, yielding 230 g (70%).

$^1$H-NMR (500 MHz, d$_6$-DMSO): d=1.88 (m, 2H); 2.36 (bs, 4 H); 2.44 (t, 2H); 3.57 (m, 4H); 3.70 (s, 3H); 3.86 (m, 4H); 4.04 (t, 2H); 6.65 (bs, 2H); 6.69 (d, 1H); 7.40 (d, 1H).

Example 6

Step A7: Preparation of 2-aminopyrimidine-5-carboxylic acid (6b)

1 kg of methyl 3,3-dimethoxypropanoate was dissolved in 7 L of 1,4-dioxane. 1.58 kg of sodium methoxide solution (30 w % in methanol) were added. The mixture was heated to reflux, and ap. 4.9 kg of distillate were removed. The resulting suspension was cooled to r.t., and 0.5 kg of methyl formate was added. The reaction mixture was stirred overnight, then 0.71 kg of guanidine hydrochloride was added, and the reaction mixture was stirred at r.t. for 2 h. The reaction mixture was then heated to reflux, and stirred for 2 h. 13.5 L of water were added, followed by 0.72 kg of aqueous sodium hydroxide solution (45 w %). The reaction mixture was heated at reflux for additional 0.5 h, and then cooled to 50° C. 0.92 kg of aqueous hydrochloric acid (25 w %) were added until pH 6 was reached. Seeding crystals were added, and additional 0.84 kg of aqueous hydrochloric acid (25 w %) were added at 50° C. until pH 2 was reached. The mixture was cooled to 20° C. and stirred overnight. The suspension was filtered, the collected solids washed twice with water, then twice with methanol, yielding 0.61 kg (65%).

Four batches produced according to the above procedure were combined (total 2.42 kg). 12 L of ethanol were added, and the resulting suspension was stirred at r.t. for 2.5 h. The mixture was filtered. The collected solids were washed with ethanol and dried in vacuum to yield 2.38 kg.

To 800 g of this material 2.5 L of dichloromethane and 4 L of water were added, followed by 1375 mL of dicyclohexylamine. The mixture was stirred for 30 min. at r.t. and filtered. The collected solids are discarded. The phases of the filtrate are separated, and the organic phase was discarded. 345 mL of aqueous sodium hydroxide solution (45 w %) were added to the aqueous phase. The aqueous phase was extracted with 2.5 L of ethyl acetate. The phases were separated and the organic phase discarded. The pH value of the aqueous phase was adjusted to pH 2 using app. 500 mL of hydrochloric acid (37 w %). The mixture was filtered, and the collected solids were washed with water and dried, yielding 405 g.

The 405 g were combined with a second batch of comparable quality (152 g). 2 L of ethyl acetate and 6 L of water were added, followed by 480 mL of aqueous sodium hydroxide solution (45 w %). The mixture was stirred at r.t. for 30 min. The phases were separated. The pH of the aqueous phase was adjusted to pH 2 with ap. 770 mL of aqueous hydrochloric acid (37 w %). The mixture was filtered, and the collected solids washed with water and dried to yield 535 g.

$^1$H-NMR (400 MHz, d$_6$-DMSO): δ=7.46 (bs, 2H); 8.66 (s, 2H), 12.72 (bs, 1H).

Example 7

Step A6: Preparation of Copanlisib (7)

A mixture of 600 g of 7-methoxy-8-[3-(morpholin-4-yl)propoxy]-2,3-dihydro-imidazo[1,2-c]quinazolin-5-amine, 306 g of 2-aminopyrimidine-5-carboxylic acid, 204 g of N,N-dimethyl-4-aminopyridine, 480 g of N-[3-(dimethylamino)propyl]-N'-ethylcarbodiimide hydrochloride and 1500 g of N,N-dimethylformamide was stirred at room temperature for 15 h. The mixture was filtered, the filter cake was washed with N,N-dimethylformamide then ethanol. The collected solids were dried in vacuum to yield 769 g of copansilib (96%).

Example 8

Step A8: Preparation of Copanlisib Dihydrochloride (8)

To a suspension of 366 g of copanlisib in 1015 g water, 183 g of an aqueous hydrochloric acid solution (32%) were added while maintaining the temperature at 20° C. (±2° C.) until a pH of 3 to 4 was reached. The resulting mixture was stirred at room temperature for more than 10 min., filtered and the filtercake washed with additional 82 g of water. The filtrate was adjusted to pH 1.8 to 2.0 using aqueous hydrochloric acid solution (32%). The mixture was stirred for 10 min. at room temperature, 146 g of ethanol (100%) were added and stirred for another 10 min. 1 g of seed crystals were added, followed by 1592 g ethanol within 5 h. The resulting substance was removed by filtration, washed with a water-ethanol mixture and dried in vacuum to give 410 g (97%) of the copanlisib dihydrochloride.

$^{1}$H-NMR (500 MHz, d$_{6}$-DMSO): δ=2.32 (m, 2H); 3.11 (m, 2H); 3.29 (m, 2H); 3.48 (m, 2H); 3.83 (m, 2H), 3.98 (m, 2H); 4.00 (s, 3H); 4.19 (t, 2H); 4.37 (t, 2H); 4.47 (t, 2H); 7.39 (d, 1H); 7.54 (s, 2H); 8.21 (d, 1H); 8.97 (s; 2H); 11.1 (bs, 1H); 12.6 (bs, 1H); 13.4 (bs, 1H).

HPLC: stationary phase: XBridge Shield (150 mm, 3.0 mm ID, 3.5 μm particle size): mobile phase A: 20 mmol sodiumdodecylsulphate and 4.0 mL phosphoric acid (85%)/1 L water; mobile phase B: 20 mmol sodiumdodecylsulphate and 4.0 mL phosphoric acid (85%)/L acetonitrile/water (8:2 V/V); UV detection at 250 and 210 nm; oven temperature: 25° C.; injection volume: 3.0 μL; flow 0.5 mL/min; linear gradient in 3 steps: 40% B->50% B (5 min), 50% B->65% B (25 min), 65% B->100% B (5 min), 10 minutes holding time at 100% B; purity: >99.7% 99.75 (Rt=27.1 min), relevant potential by-products: 2-Aminopyrimidine-5-carboxylic acid at RRT (relative retention time) of 0.09 (2.4 min) typically <0.10%, 4-dimethylaminopyrimidine RRT 0.28 (7.6 min): typically <0.03%, by-product 1 RRT 1.03 (27.8 min): typically <0.03%, 7-methoxy-8-(3-morpholin-4-ylpropoxy)-2,3-dihydroimidazo[1,2-c]quinazolin-5-amine RRT 1.14 (31.0 min): typically <0.03%, by-product 6 RRT 1.24 (33.6 min): typically <0.15%, Additional HPLC method to determine 2-amino-N-{3-(2-aminoethyl)-8-methoxy-7-[3-(morpholin-4-yl)propoxy]-4-oxo-3,4-dihydroquinazolin-2-yl}pyrimidine-5-carboxamide pyramide: stationary phase: XBridge Shield (150 mm, 3.0 mm ID, 3.5 μm particle size): mobile phase A:: 2.0 mL trifluoro acetic acid/1 L water; mobile phase B: 2.0 mL trifluoro acetic acid/L acetonitrile; UV detection at 250 nm; oven temperature: 20° C.; injection volume: 1.0 μL; flow 0.5 mL/min; li near gradient in 2 steps: 0% B->25% B (20 min), 25% B->35% B (5 min), 5 minutes holding time at 35% B; BAY 80-6946 Rt=15.0 min, 2-amino-N-{3-(2-aminoethyl)-8-methoxy-7-[3-(morpholin-4-yl)propoxy]-4-oxo-3,4-dihydroquinazolin-2-yl}pyrimidine-5-carboxamide RRT 1.07 (16.5 min): typically <0.10%.

The invention claimed is:

1. A method of preparing copanlisib (7):

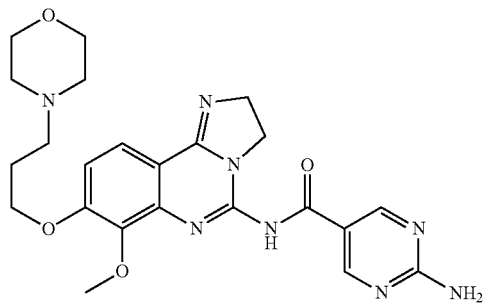

comprising the following steps:

step A6:

reacting a compound of formula (6):

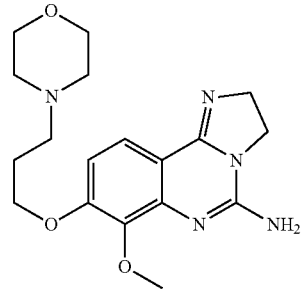

with a compound of formula (6b):

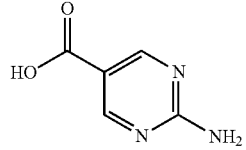

in the presence of a catalyst and a coupling agent, to provide copanlisib (7):

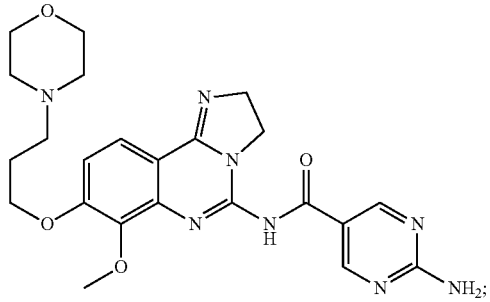

wherein the compound of formula (6):

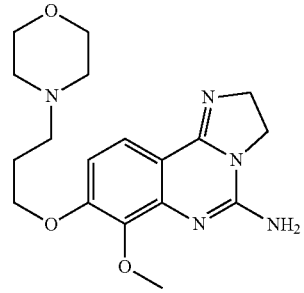

is prepared by the following step A5:
reacting a compound of formula (5):

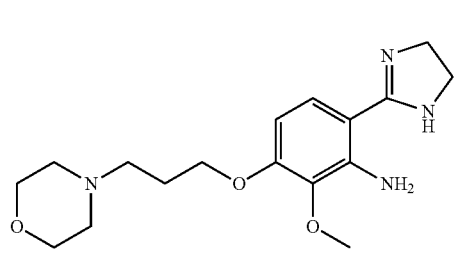
(5)

with cyanogen bromide as annelating agent,
to provide the compound of formula (6);
wherein the compound of formula (5):

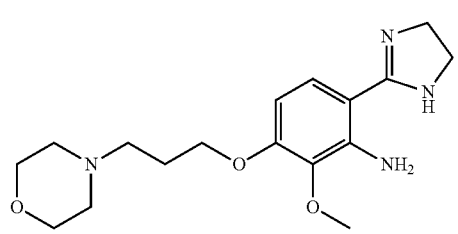
(5)

is prepared by the following step A4:
reacting a compound of formula (4):

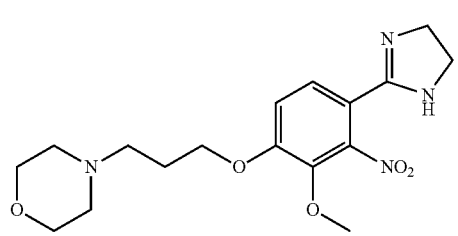
(4)

with hydrogen in the presence of a 5% palladium/1% iron catalyst on carbon which is water-wetted, in a solvent, to provide the compound of formula (5).

2. The method according to claim 1, wherein the compound of formula (4):

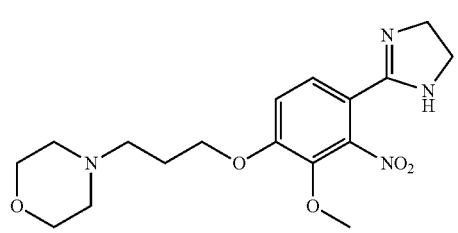
(4)

is prepared by the following step A3:
reacting a compound of formula (3):

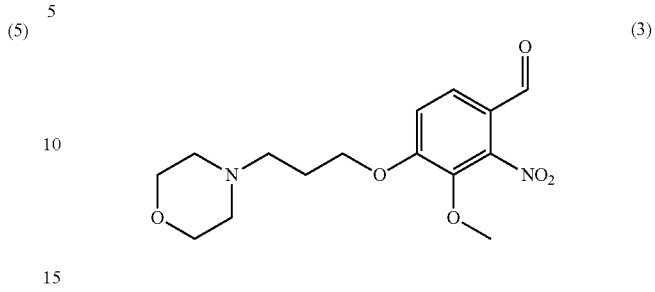
(3)

with ethylenediamine to provide the compound of formula (4).

3. The method according to claim 2, wherein the compound of formula (3):

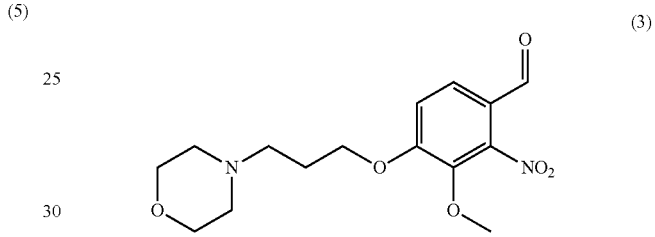
(3)

is prepared by the following step A2:
reacting a compound of formula (2):

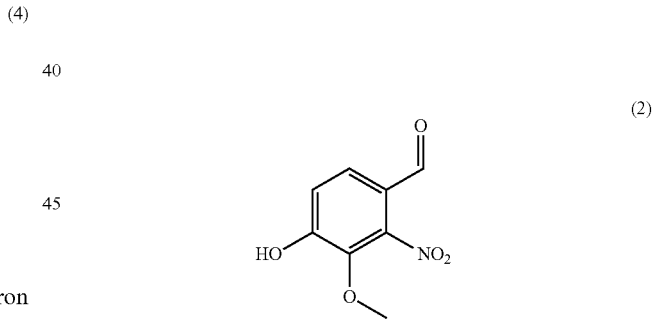
(2)

with a compound of formula (2a):

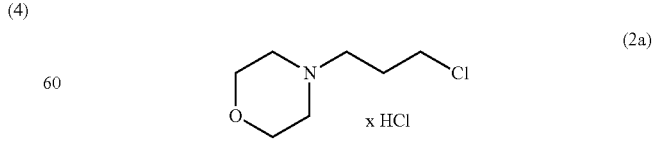
(2a)

to provide the compound of formula (3).

4. The method according to claim 3, wherein the compound of formula (2):

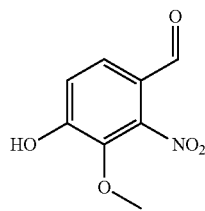
(2)

is prepared by the following step A1:
a) reacting a compound of formula (1):

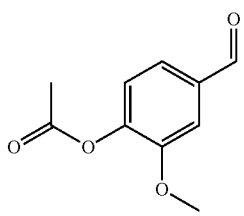
(1)

with nitric acid and sulphuric acid to form a reaction mixture, and
b) adding a base to the reaction mixture of a) to provide the compound of formula (2).

5. The method according to claim 1, wherein the compound of formula (6b):

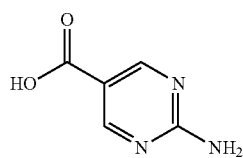
(6b)

is prepared by the following step A7:
a) reacting a compound of formula (6a):

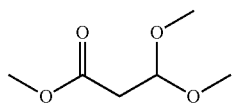
(6a)

with a base, with heating, to form a reaction mixture;
b) cooling the reaction mixture from a), and adding methyl formate to the resulting reaction mixture;
c) adding guanidine hydrochloride to the reaction mixture from b), followed by heating;
d) adding water and an aqueous solution of a base to the reaction mixture from c), followed by heating;
e) adding an aqueous solution of a mineral acid to the reaction mixture from d);
f) adding an amine to the reaction mixture from e), and filtering off a resulting solid;
g) adding an aqueous solution of a strong base to the reaction mixture from f); and
h) adding an aqueous solution of a mineral acid to the reaction mixture from g), to provide the compound of formula (6b):

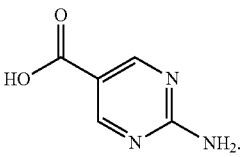
(6b)

6. The method according to claim 1, further comprising the following step A8:

reacting copanlisib (7):

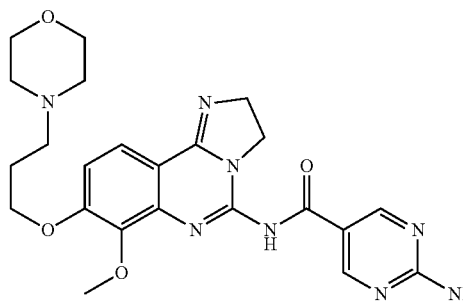
(7)

with hydrogen chloride
to provide copanlisib dihydrochloride (8):

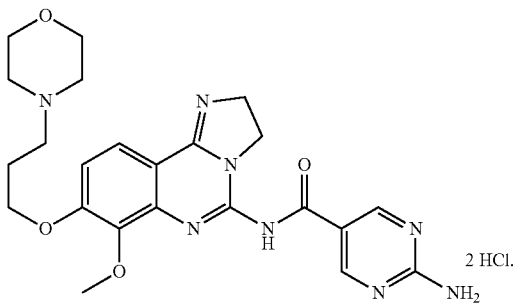
(8)

7. The method according to claim 1, wherein copanlisib (7) is prepared by the following steps shown in Reaction Scheme 3:

Reaction Scheme 3:
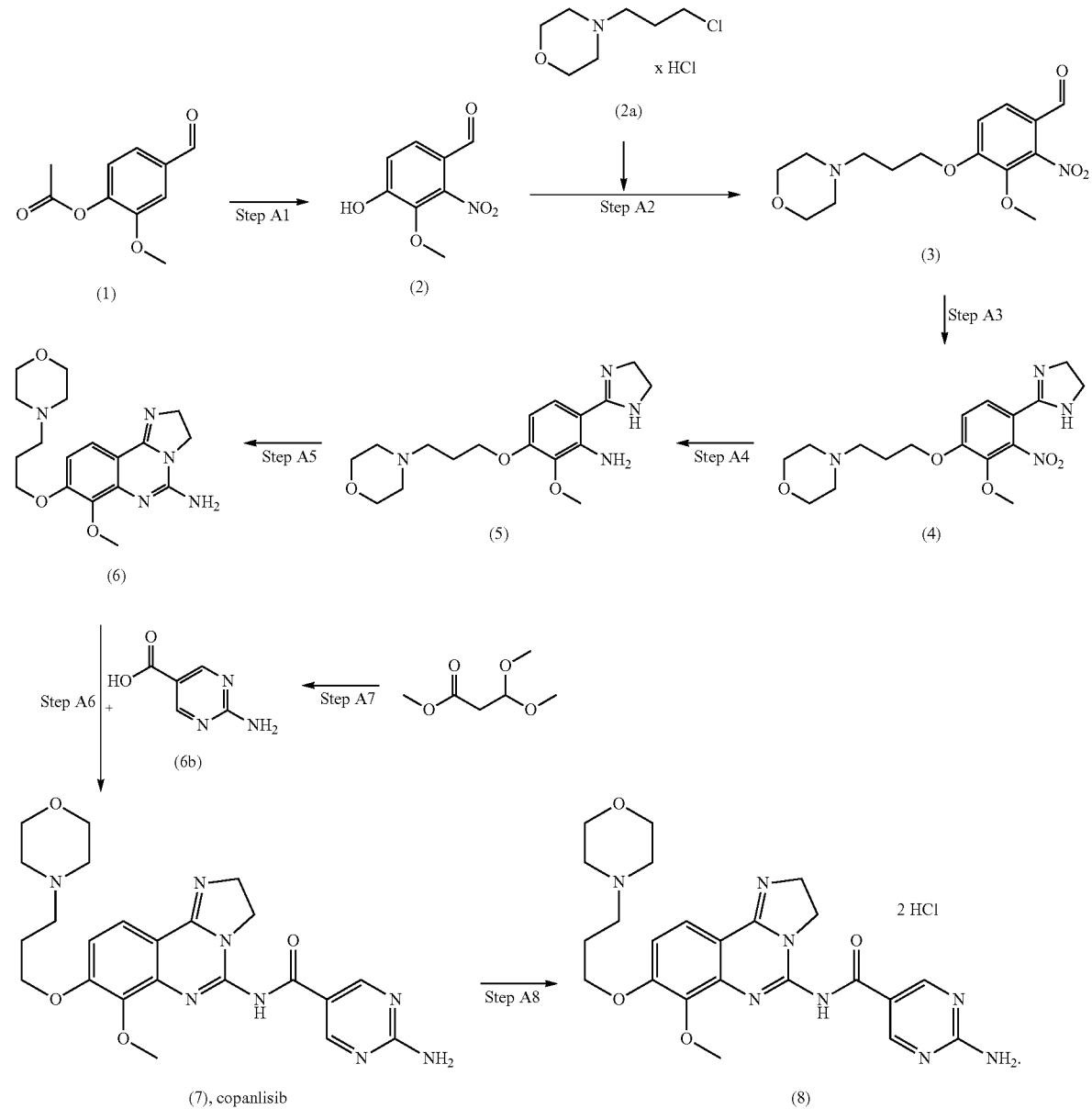
8. A compound selected from the group consisting of:
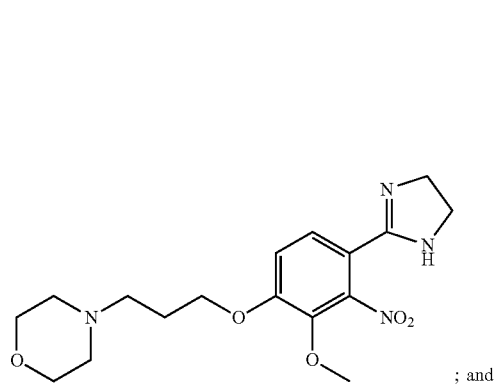
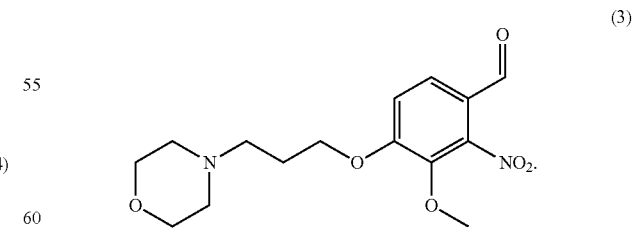
9. The method of claim 1, wherein the catalyst of step A6 is N,N-dimethyl-4-aminopyridine.
10. The method of claim 1, wherein the coupling agent of step A6 is N-[3-(dimethylamino)propyl]-N'-ethylcarbodiimide hydrochloride.

11. The method of claim 1, wherein step A5 is carried out in the presence of a base, and wherein the base is triethylamine.

12. The method of claim 3, wherein step A2 is carried out in the presence of a base, and wherein the base is potassium carbonate.

13. The method of claim 4, wherein the base of step A1 b) is potassium carbonate.

14. The method of claim 5, wherein the base of step A7 a) is sodium methoxide.

15. The method of claim 5, wherein the base of step A7 d) is sodium hydroxide.

16. The method of claim 5, wherein the mineral acid of step A7 e) is hydrochloric acid.

17. The method of claim 5, wherein the amine of step A7 f) is dicyclohexylamine.

18. The method of claim 5, wherein the strong base of step A7 g) is sodium hydroxide.

19. The method of claim 5, wherein the mineral acid of step A7 h) is hydrochloric acid.

20. The method of claim 2, wherein step A3 is carried out in the presence of N-bromosuccinimide.

21. The method of claim 1, wherein step A6 is carried out in the presence of a solvent, and wherein the solvent is N,N-dimethylformamide.

22. The method of claim 1, wherein step A5 is carried out in the presence of a solvent, and wherein the solvent is dichloromethane.

23. The method of claim 1, wherein the solvent of step A4 is methanol.

24. The method of claim 2, wherein step A3 is carried out in the presence of a solvent, and wherein the solvent is dichloromethane.

25. The method of claim 3, wherein step A2 is carried out in the presence of a solvent, and wherein the solvent is acetonitrile.

* * * * *